United States Patent
Akira (10) Patent No.: US 7,329,795 B2
(45) Date of Patent: Feb. 12, 2008

(54) MODEL ANIMALS NON-RESPONSIVE TO MYCOBACTERIAL-ORIGIN LIPOPROTEIN/LIPOPEPTIDE

(75) Inventor: Shizuo Akira, Osaka (JP)

(73) Assignee: Japan Science and Technology Agency, Kawaguchi-Shi, Saitama (JP)

( * ) Notice: Subject to any disclaimer, the term of this patent is extended or adjusted under 35 U.S.C. 154(b) by 0 days.

(21) Appl. No.: 10/517,663

(22) PCT Filed: Dec. 10, 2002

(86) PCT No.: PCT/JP02/12908

§ 371 (c)(1),
(2), (4) Date: Aug. 31, 2005

(87) PCT Pub. No.: WO03/105578

PCT Pub. Date: Dec. 24, 2003

(65) Prior Publication Data

US 2006/0059579 A1    Mar. 16, 2006

(30) Foreign Application Priority Data

Jun. 13, 2002  (JP) .............................. 2002-173254

(51) Int. Cl.
*A01K 67/027*  (2006.01)
*G01N 33/00*  (2006.01)
(52) U.S. Cl. .......................................... 800/18; 800/3
(58) Field of Classification Search .................. 800/13
See application file for complete search history.

(56) References Cited

FOREIGN PATENT DOCUMENTS

JP          2002-45086 A    2/2002

OTHER PUBLICATIONS

Takeuchi et al, International Immunopharmacology, 1:625-635, 2001.*
Thoma-Uszynski et al, Science, 291:1544-1547, 2001.*
Takeuchi et al, The Journal of Immunology, 169:10-14, 2002.*
Takeuchi et al, International Immunology, 13:933-940, 2001.*
Takeuchi, International Immunopharmacology, 1:625-635, 2001.*
Cole, Nature, 393:537-544, 1989.*
Houdebine, Journal of Biotechnology, 98:145-160, 2002.*
Smith, Journal of Biotechnology, 99:1-22, 2002.*
Alexopoulou et al, Nature Medicine, 8:878-884, 2002.*
Henneke et al, Journal of Immunology, 167:7069-7076, 2001.*
Osamu Takeuchi et al., "Cutting Edge: Role of Toll-Like Receptor 1 in Mediating Immune Response to Microbial Lipoproteins", The Journal of Immunology, Jul. 1, 2002, pp. 10-14, vol. 169, No. 1.
Lena Alexopoulou et al., Hyporesponsiveness to Vaccination with *Borrelia burgdorferi* OspA in Humans and TLR1- and TLR2-Deficient Mice, Nature Medicine, Aug. 2002, pp. 878-884, vol. 8, No. 8.
Osamu Takeuchi, "Toll-Like Receptor Knockout Mouse", Cell Technology, Apr. 22, 2000, pp. 767-774, vol. 19, No. 5.
Adeline M. Hajjar et al., Cutting Edge: Functional Interactions Between Toll-Like Receptor (TLR) 2 and TLR1 or TLR6 in Response to Phenol-Soluble Modulin, The Journal of Immunology, Jan. 1, 2001, pp. 15-19, vol. 166, No. 1.

* cited by examiner

*Primary Examiner*—Valarie Bertoglio
(74) *Attorney, Agent, or Firm*—Robert Kinberg; Ann S. Hobbs; Venable LLP (57) ABSTRACT

The present invention is to provide TLR1 knockout mice specifically recognizing mycobacterial lipoproteins/lipopeptides, being useful to clarify the role of TLR1 in vivo, or a method for screening substances promoting or suppressing the response to mycobacterial lipoproteins/lipopeptides by using the same. TLR1 genes are separated from murine genomic library, the genomic part containing the intracellular and transmembrane domain of the TLR1 gene is replaced with a neomycin resistant gene, HSV-tk gene being gene encoding thymidine kinase into 3' end is introduced, ES cell clones having double resistance to G418 and Gancyclovir are screened, and ES cell clones are injected into the blastocyst of C57BL/6 mice, to generate TLR1 knockout mice through the germline.

2 Claims, 8 Drawing Sheets

MODEL ANIMALS NON-RESPONSIVE TO MYCOBACTERIAL-ORIGIN LIPOPROTEIN/LIPOPEPTIDE

TECHNICAL FIELD

The present invention relates to an non-human animal model non-responsive to mycobacterial lipoproteins/lipopeptides, wherein the function of the gene encoding proteins such as TLR1, specifically recognizing mycobacterial lipoproteins/lipopeptides is deleted on its chromosome, or to a method for screening substances promoting or suppressing response to mycobacterial lipoproteins/lipopeptides, or the like.

BACKGROUND ART

Toll genes are associated with the determination of dorsoventral axis in the embryogenesis of *Drosophilia* (Cell 52, 269-279, 1988; Annu. Rev. Cell Dev. Biol. 12, 393-416, 1996), and with innate immunity detecting invading pathogens in adult body (Nature 406, 782, 2000; Nat. Immunol. 2, 675, 2001; Annu. Rev. Immunol. 20, 197, 2002). It has been clarified the Toll is a type I-transmembrane receptor having Leucine-rich repeat (LRR) in the extracellular domain, and that the intracytoplasmic domain is highly homologous with the intracytoplasmic domain of mammal-Interleukin-1 receptor (IL-1R) (Nature 351, 355-356, 1991; Annu. Rev. Cell Dev. Biol., 12, 393-416, 1996; J. Leukoc. Biol. 63, 650-657, 1998).

Recently, mammal homologue of Toll has been identified, that is the Toll Like Receptor (TLR) (Nature 388, 394-397, 1997; Proc. Natl. Acad. Sci. USA95, 588-593, 1998; Blood 91, 4020-4027, 1998; Gene 231, 59-65, 1999) and 10 members of human TLR family such as TLR2 and TLR4 have been reported so far. The role of TLR family is to recognize discrete pathogen-associated molecular patterns (PAMPs) as pattern recognition receptor (PRR) recognizing common bacterial structure, to trigger the activation of similar intracellular signaling pathway leading to the nuclear translocation of a transcription factor, NF-κB. The signaling pathway ultimately culminates in the production of inflammatory cytokines to evoke host defense responses and further evoke host defense responses to acquired immunity. Moreover, various TLR ligands are reported recently.

TLR2 recognizes a variety of bacterial components, such as peptidoglycan (PGN), bacterial tri-acylated lipoproteins, mycoplasmal di-acylated lipoproteins, and GPI anchor of *Trypanosoma cruzi* (Science 285, 732, 1999; Science 285, 736, 1999; J. Biol. Chem. 274, 33419, 1999; Immunity 11, 443, 1999; J. Immunol. 164. 554, 2000; Nature 401, 811, 1999; J. Immunol. 167, 416, 2001). TLR4 is essential for responses to LPS, a glycolipid specific to Gram-negative bacteria cell wall. TLR5 is reported to recognize flagellin, a protein component of bacterial flagella. Furthermore, nucleotides specific to pathogens and nucleotide analogues are also detected by TLRs. In other words, TLR 3, TLR 7 and TLR 9 participate in the recognizition of viral double stranded RNA, imidazoquinolines and bacterial DNA with unmethylated CpG motif, respectively (Nature 406, 782, 2000; Nat. Immunol. 2, 675, 2001; Annu. Rev. Immunol. 20, 197, 2002; Nat. Immunol. 3, 196, 2002).

As TLRs can form heterodimers, their ligand specificity can be further defined. Notably, TLR6 has a unique property to recognize a mycoplasmal lipoprotein by interacting with TLR2 (Proc. Natl. Acad. Sci. USA 97, 13766, 2000; Int. Innmunol. 13, 933, 2001). TLR6-deficient mice (TLR6$^{-/-}$) do not respond to di-acylated mycoplasmal lipopeptides, termed macrophage-activating lipopeptide 2-kD (MALP-2), and do not produce inflammatory cytokines. On the other hand, TLR6-deficient mice respond normally to a tri-acylated bacterial lipopeptide. TLR2$^{-/-}$ macrophages do not respond to neither of these lipopeptides (Int. Immuno. 13, 933, 2001). That is, it becomes clear that TLR6 discriminates a subtle difference in the acylization of lipopeptides derived frommicrobial pathogens. Furthermore, these findings raise the possibility that TLR2 forms a heterodimer with a different TLR to recognize other PAMPs in the tri-acylated lipopeptides.

On the other hand, lipoproteins are produced by a variety of pathogens including mycobacteria, Gram-negative bacteria and mycoplasma species (Microbiol. Rev. 60, 316, 1996). The N-terminus acylated lipopeptide region is responsible for the immunostimulatory activity of bacterial and mycoplasmal lipoproteins. Bacterial and mycoplasmal lipoproteins differ in the degree of acylation of N-terminus cysteine. Lipoproteins of bacteria are tri-acylated, whereas those of mycoplasma are di-acylated (Trends Microbiol. 7, 493, 1999). Synthetic lipoprotein analogue consisting of a palmitoyled version of N-acyl-S-diacyl cysteine and S-diacyl cysteine mimic the immunostimulatory activity of bacterial and mycoplasmal lipoprotein, respectively (Immunobiology 177, 158, 1988; J. Exp. Med. 185, 1951, 1997).

TLR1 shows high similarity with TLR6 (Gene 231, 59, 1999). It was reported that overexpression of TLR1 inhibited the TLR2-mediated responses to modulin which are phenol-soluble proteins secreted from *Staphylococcus epidermidis* (J. Immunol. 166, 15, 2001). On the other hand, another report showed that TLR1 participates in the recognition of soluble factors from *Neisseria meningitides* (J. Immunol. 165, 7125, 2000). However, the ligand of TLR1 in vivo is yet to be clarified.

The response to bacterial components in vivo is estimated to vary upon the difference of the expression level of each TLR on the surface of the cells, but the involvement of each member of TLR family to the signaling by the stimulation of bacterial components in vivo is not yet clarified. Moreover, it was known that water-insoluble lipoprotein/lipopeptide existing in biomembranes and the like activates immunocytes. However, no protein specifically recognizing mycobacterial lipoproteins/lipopeptides was known. The object of the present invention is to provide non-human animal model non-responsive to mycobacterial lipoproteins/lipopeptides wherein the function of the gene encoding specifically mycobacterial lipoproteins/lipopeptides, useful to clarify the involvement of each member of TLR family to the signaling by stimulation of mycobacterial lipoproteins/lipopeptides, especially the in vivo function of TLR1, is deleted on its chromosome, especially a non-human animal wherein the function of TLR1 gene is deleted on its chromosome, and a method for screening substances promoting or suppressing response to mycobacterial lipoproteins/lipopeptides by using these.

DISCLOSURE OF THE INVENTION

The present inventors isolated TLR1 genes already identified from murine genomic library, substituted the gene site including the intracellular and transmembrane domain of the TLR1 gene to a neomycin-resistant gene, introduced HSV-tk gene, a gene encoding thymidine kinase, on each of 3' end, screened ES cells clones having double resistance to both G418 and Ganciclovir. The ES cell clones were injected into C57BL/6 mice blastocysts, and TLR1 knockout mice wherein the TLR1 gene function is deleted on its chromosome were obtained according to the Mendel law through the germline. By comparing and analyzing the TLR1 knockout mice with wild-type and TLR2 knockout mice, they confirmed that TLR1 is a receptor protein specifically recognizing mycobacterial lipoproteins/lipopeptides. The present invention has been thus completed.

In other words, the present invention relates to a non-human animal model non-responsive to mycobacterial lipoproteins/lipopeptides, wherein the function of the gene encoding a protein specifically recognizing mycobacterial lipoproteins/lipopeptides is deleted on its chromosome ("1"); the non-human animal model non-responsive to mycobacterial lipoproteins/lipopeptides according to "1", wherein the function of the gene encoding a protein specifically recognizing synthesized tri-acylated lipopeptides is deleted on its chromosome ("2"); the non-human animal model non-responsive to mycobacterial lipoproteins/lipopeptides according to "2", wherein the synthetic tri-acylated lipopeptide is a N-palmitoyl-S-dilaurylglyceryl ("3"); the non-human animal model non-responsive to mycobacterial lipoproteins/lipopeptides according to any one of "1" to "3", wherein the protein specifically recognizing mycobacterial lipoproteins/lipopeptides is TLR1 ("4"); the non-human animal model non-responsive to mycobacterial lipoproteins/lipopeptides according to any one of "1" to "4", wherein the non-human animal is a rodent ("5"); the non-human animal model non-responsive to mycobacterial lipoproteins/lipopeptides according to "5", wherein the rodent is a mouse ("6"); the non-human animal model non-responsive to mycobacterial lipoproteins/lipopeptides according to "6", wherein the mouse is a TLR1 knockout mouse generated by constructing a targeting vector by substituting a whole or a part of the gene fragment of the gene site including the intracellular and transmenbrane domain of the TLR1 gene, obtained from screening TLR1 genes from murine genomic library by using a probe from mouse EST clones; by linearizing the targeting vector and injecting it into embryonic stem cells, by microinjecting the targeted stem cells wherein the TLR1 gene function is deleted into the mouse blastocysts to generate chimeric mice; by breeding the chimeric mice and wild-type mice to generate heterozygous mice; and by intercrossing the heterozygous mice ("7"); and a method for screening substances promoting or suppressing response to mycobacterial lipoproteins/lipopeptides, wherein the response to mycobacterial lipoproteins/lipopeptides in the immunocytes derived from non-human animal non responsive to mycobacterial lipoproteins/lipopeptides according to any one of "1" to "7" is measured/estimated, by using the immunocytes, a test substance and a mycobacterial lipoprotein/lipopeptide ("8").

Furthermore, the present invention relates to a method for screening substances promoting or suppressing the response to mycobacterial lipoproteins/lipopeptides, wherein the response to mycobacterial lipoproteins/lipopeptides of the non-human animal non-responsive to mycobacterial lipoproteins/lipopeptides according to any one of "1" to "7" is measured/estimated by using the non-human animal, a test substance and a mycobacterial lipoprotein/lipopeptide ("9"); the method for screening substances promoting or suppressing the response to mycobacterial lipoproteins/lipopeptides according to "8" or "9", wherein the comparison/estimation with a wild-type non-human animal of its littermate is performed as a control when measuring/estimating response to mycobacterial lipoproteins/lipopeptides ("10"); the method for screening substances promoting or suppressing the response to mycobacterial lipoproteins/lipopeptides according to any one of "8" to "10", wherein the substance promoting or suppressing the response to mycobacterial lipoproteins/lipopeptides is an agonist or an antogonist to TLR1 ("11"); the method for screening substances promoting or suppressing the response to mycobacterial lipoproteins/lipopeptides according to any one of "8" to "11", wherein the substance promoting response to mycobacterial lipoproteins/lipopeptides is a therapeutic/preventive agent for mycobacterial infection ("12"); the method for screening substances promoting or suppressing the response to mycobacterial lipoproteins/lipopeptides according to "12", wherein the mycobacterial infection is tuberculous or a mycobacterial infection other than tuberculous ("13"); a substance promoting or suppressing the response to mycobacterial lipoproteins/lipopeptides, obtained by the method for screening a substance promoting or suppressing the response to mycobacterial lipoproteins/lipopeptides according to any one of "8" to "13" ("14"); the substance promoting or suppressing the response to mycobacterial lipoproteins/lipopeptides according to "14", wherein the substance promoting or suppressing the response to mycobacterial lipoproteins/lipopeptides is an agonist or antagonist to TLR1 ("15"); the substance promoting or suppressing the response to mycobacterial lipoproteins/lipopeptides according to "14" or "15", wherein the substance promoting the response to mycobacterial lipoproteins/lipopeptides is a therapeutic/preventive agent for mycobacterial infection ("16"); the substance promoting or suppressing the response to mycobacterial lipoproteins/lipopeptides according to "15", wherein the mycobacterial infection is tuberculous or a mycobacterial infection other than tuberculous ("17").

Furthermore, the present invention relates to a therapeutic/preventive agent for mycobacterial infection containing TLR1 and TLR2 expression systems ("18"); the therapeutic/preventive agent for mycobacterial infection according to "18", wherein the mycobacterial infection is tuberculous or a mycobacterial infection other than tuberculous ("19").

BEST MODE FOR CARRYING OUT THE INVENTION

As for a non-human animal model non-responsive to mycobacterial lipoproteins/lipopeptides of the present invention, there is no specific limitation as long as it is an animal model other than human, wherein the function of the gene encoding a protein specifically recognizing mycobacterial lipoproteins/lipopeptides is deleted on its chromosome, but it is preferable that it is an animal model other than human, wherein the function of the gene encoding a protein specifically recognizing not only mycobacterial lipoproteins/lipopeptides but also synthetic tri-acylated lipopeptides such as N-palmitoyl-S-dilaurylglyceryl, is deleted on its chromosome. For example, by a gene mutation such as destruction, deletion or substitution of a whole or a part of an endogenous gene from a non-human animal encoding a protein specifically recognizing mycobacterial lipoproteins/lipopeptides to inactivate its function, the function of the gene encoding a protein specifically recognizing mycobacterial lipoproteins/lipopeptides can be deleted on its chromosome. Moreover, as for the above-described protein specifically recognizing mycobacterial lipoproteins/lipopeptides, there is no specific limitation as long as it is a protein that can specifically recognize mycobacterial lipoproteins/lipopeptides, and examples include TLR1 or a part thereof having TLR1 activation. The protein specifically recognizing mycobacterial lipoprotein/lipopeptide can be prepared by a known method according to its DNA sequence information and the like. Furthermore, mycobacterial lipoproteins/lipopeptides of the present invention include, for convenience, lipoproteins/lipopeptides derived from Mycobacteria as well as mycobacterial cells itself, or their disposal, synthetic mycobacterial lipopeptides such as MALP-2.

The non-human animal model non-responsive to mycobacterial lipoproteins/lipopeptides of the present invention refers to non-human animals, wherein the responsiveness of the living body or of the cells, tissues or organs composing the living body against mycobacterial lipoproteins/lipopeptidestimulation, is specifically reduced or deleted, compared to that of wild-type mouse. In other words, it is related to non-human animals such as mice, rats and rabbits, wherein the responsiveness of the living body or of the cells, tissues or organs composing the living body is normal to lipoproteins/lipopeptides other than Mycobacteria such as spirochete or Gram-negative bacteria, whereas the responsiveness of the living body or of the cells, tissues or organs composing the living body to mycobacterial lipoproteins/lipopeptides is reduced or deleted. For instance, non-human animals such as TLR1 knockout mouse, wherein the function of TLR1 gene is deleted on its chromosome can be exemplified. Moreover, as for the above-mentioned stimulation by mycobacterial lipoproteins/lipopeptides, in vivo stimulation administering mycobacterial lipoproteins/lipopeptides in the living body, or in vitro stimulation contacting mycobacterial lipoproteins/lipopeptides to cells separated from the living body can be exemplified.

Next, the method for preparing non-human animal model non-responsive to mycobacterial lipoproteins/lipopeptides of the present invention will be explained by taking TLR1 knockout mouse as an example. With the use of a gene fragment obtained by PCR method or the like from murine genomic library, genes encoding TLR1 are screened, and the screened genes encoding TLR1 are subcloned by using viral vectors and the like and are identified by DNA sequencing. A whole or a part of the gene encoding TLR1 is replaced with pMC1 neo-gene cassette and the like, and targeting vectors are prepared by introducing genes such as Dyphtheria-toxin A fragment (DT-A) or herpes simplex virus thymidine kinase (HSV-tk) genes to 3' end.

The prepared targeting vector is linearized and introduced into ES cells by electroporation and the like for homologous recombination, and ES cells having performed homologous recombination by antibiotics such as G418 or Gancyclovir (GANC) are selected from homologous recombinants. Moreover, it is preferable to confirm if the selected ES cells as the desired recombinants by Southern blot method or the like. Clones of the confirmed ES cells are microinjected into mouse blastocysts which are returned to recepient mice, to generate chimeric mice. The chimeric mice are bred to wild-type mice to obtain heterozygous mice (F1 mice: +/−), and by breeding the heterozygotes, TLR1 knockout mice of the present invention are generated. Moreover, as for a method for confirming whether TLR1 has emerged in TLR1 knockout mice, a method by isolating RNA from a mouse obtained by the above-mentioned method and examining by Northern Blot method or the like, or a method by investigating TLR1 expression of the mice can be investigated by Western Blot method or the like, can be exemplified.

Furthermore, it can be confirmed that the generated TLR1 knockout mice are non-responsive to mycobacterial lipoproteins/lipopeptides, by for example contacting mycobacterial lipoproteins/lipopeptides to immunocytes such as macrophages, mononuclear cells, dendritic cells, in vitro or in vivo, and by measuring the production levels of TNF-α, IL-6, IL-12, IFN-γ and the like in said cells, the proliferative response of splenic B cells, the expression level of antigens such as CD 40, CD80, CD86, MHC class II on the surface of splenic B cells, or the activation of molecules in the signaling pathway such as NF-κB, JNK, IRAK. Therefore, the TLR1 knockout mice of the present invention can be a useful model to elucidate the effect mechanism of mycobacterial lipoproteins/lipopeptides or to investigate a treatment strategy to mycobacterial infection.

In the meantime, among homozygous non-human animal generated upon Mendel's law, animals wherein the protein specifically recognizing mycobacterial lipoproteins/lipopeptides is deleted and wild-types animals being its littermates are included. By using at the same time the deficient-types and wild-types being its littermate of the homologous non-human animals, it is possible to conduct accurate comparative examples at individual levels. Therefore, for example, when screening substances promoting or suppressing the response to mycobacterial lipoproteins/lipopeptides of the present invention as described in the following, it is preferable to use wild-type non-human animals, preferably wild-type non-human animals of the same species than that of non-human animals wherein the function of the gene encoding a protein specifically recognizing Mycobacteria lipoproteins/lipopeptides is deleted on its chromosome, and its littermates at the same time.

Non-human animal models non-responsive to mycobacterial lipoprotein/lipopetide of the present invention, or immunocytes such as macrophages, splenic cells, dendritic cells derived from said non-human model animals can be used for example for screening substances promoting or suppressing the response to mycobacterial lipoproteins/lipopeptides of the present invention such as agonists or antagonists to TLR1, or for screening preventive/treating agents for mycobacterial infections such as pulmonary tuberculosis, beside for elucidating the effect mechanism of mycobacterial lipoproteins/lipopeptides. The method for screening substances promoting or suppressing the response to mycobacterial lipoproteins/lipopeptides such as agonists or antagonists to TLR1 will be explained in the following by referring to the examples.

As for the method for screening substances promoting or suppressing the response to mycobacterial lipoproteins/lipopeptides of the present invention, it can be exemplified by a method for measuring/estimating the response to mycobacterial lipoproteins/lipopeptides in immunocytes such as macrophages, splenic cells or dendritic cells derived from non-human animal models non-responsive to mycobacterial lipoproteins/lipopeptides, by using the immunocytes, a test substance and mycobacterial lipoproteins/lipopeptides; or a method for measuring/estimating the response to mycobacterial lipoproteins/lipopeptides in non-human model animal non-responsive to mycobacterial lipoproteins/lipopeptides, by using the non-human animal model, a test substance and mycobacterial lipoproteins/lipopeptides.

As for a method for screening by using immunocytes derived from non-human animal models non-responsive to mycobacterial lipoproteins/lipopeptides described above, a method comprising the steps to contact previously the immunocytes obtained from non-human animal model non-responsive to mycobacterial lipoproteins/lipopeptides with a test substance in vitro, to culture the immunocytes in the presence of mycobacterial lipoproteins/lipopeptides and to measure/estimate the response to mycobacterial lipoproteins/lipopeptides in the immunocytes; or a method comprising the steps to contact previously the immunocytes obtained from non-human model animal non-responsive to mycobacterial lipoproteins/lipopeptides with mycobacterial lipoproteins/lipopeptides in vitro, to culture the immunocytes in the presence of a test substance, and to measure/estimate the response to mycobacterial lipoproteins/lipopeptides in the immunocytes can be exemplified.

Furthermore, a method comprising the steps to administer previously a test substance to a non-human model animal non-responsive to mycobacterial lipoproteins/lipopeptides, to culture the immunocytes obtained from the non-human model animals in the presence of mycobacterial lipoproteins/lipopeptides, and to measure/estimate the response to mycobacterial lipoproteins/lipopeptides in the immunocytes; or a method comprising the steps to administer previously a test substance to a non-human animal model non-responsive to mycobacterial lipoproteins/lipopeptides of the present invention, to administer mycobacterial lipoproteins/lipopeptides to the non-human animal, and to measure/estimate the response to mycobacterial lipoproteins/lipopeptides in the immunocytes obtained from the non-human animals, can be exemplified.

Moreover, a method comprising the steps to administer previously mycobacterial lipoproteins/lipopeptides to a non-human animal model non-responsive to mycobacterial lipoproteins/lipopeptides of the present invention, to culture the immunocytes obtained from the non-human animal in the presence of a test substance, and to measure/estimate the response to mycobacterial lipoproteins/lipopeptides in the immunocytes; or a method comprising the steps to administer previously mycobacterial lipoproteins/lipopeptides to a non-human animal model non-responsive to mycobacterial lipoproteins/lipopeptides of the present invention, to administer a test substance to the non-human animal, and to measure/estimate the response to mycobacterial lipoproteins/lipopeptides in the immunocytes obtained from the non-human animal can be exemplified.

Further, as for a method for measuring/estimating the response to mycobacterial lipoproteins/lipopeptides in non-human model animals non-responsive to mycobacterial lipoproteins/lipopeptides of the present invention, by using the non-human animal model, a test substance, and a mycobacteria, a method comprising the steps to administer previously a test substance to a non-human animal model non-responsive to mycobacterial lipoproteins/lipopeptides, to infect the non-human animal model with Mycobacteria, and to measure/estimate the response to mycobacterial lipoproteins/lipopeptides in the non-human model animals; or a method comprising the steps to infect previously the non-human animal model non-responsive to mycobacterial lipoproteins/lipopeptides with Mycobacteria, to administer a test substance to the non-human animal model, and to measure/estimate the response to mycobacterial lipoproteins/lipopeptides in the non-human animal model, can be exemplified.

In the present invention, measurement/estimation of the response to mycobacterial lipoproteins/lipopeptides refers to a measurement/estimation of the function of reacting specifically with mycobacterial lipoproteins/lipopeptides and transmitting the signal to the cells, and as for the function for transmitting the signals, examples include the function generating cytokines such as TNF-α, IL-6, IL-12, IFN-γ; the function of generating nitrite ion; the function of proliferating cells; the function of expressing antigens such as CD40, CD80, CD86, MHC Class II on the surface of the cells; or the function of activating molecules in the signaling pathway of TLR9 such as NF-κB, JNK, IRAK, but it is not limited to these examples. Moreover, as described above, when measuring/estimating the response to mycobacterial lipoproteins/lipopeptides, it is preferable to compare/estimate with the wild-type non-human animals being its littermates as control, especially with the estimation levels of wild-type non-human animals being its littermates, to eliminate individual variety.

As it has been elucidated that TLR1 is specifically related to the recognition of mycobacterial lipoproteins/lipopeptides, by the non-human animal models wherein the responsiveness to mycobacterial lipoproteins/lipopeptides of the present invention is specifically deleted, it can be assumed that these non-human animal models can be very useful animal models to investigate treatment strategy to pulmonary or renal tuberculosis caused by *Mycobacterium tuber-* culosis. Furthermore, agonist to TLR1 can possibly be a useful substance for diagnosis/treatment of diseases caused by deletion or abnormality of TLR1 activation such as various mycobacterial infections mentioned above.

TLR1 and TLR2 interact in mammalian cells, and enhance further the responsiveness to mycobacterial lipoproteins/lipopeptides. Therefore, their co-expression in the host cells may have an effect as preventive/therapeutic agents for mycobacterial infections. As for the expression system of preventive/therapeutic agents for mycobacterial infections including the expression systems of TLR1 of the present invention and TLR2, there is no specific limitation as long as it is an expression system that can express the above-mentioned TLR1 and TLR2 in the host cells, and examples include an expression system wherein genes encoding TLR1 or TLR2 are individually integrated to viral vectors derived from papovavirus such as SV40, vaccinia virus, adenovirus, fowl poxvirus, pseudorabies virus; an expression system wherein genes encoding TLR1 or TLR2 are integrated individually; or an expression system wherein genes encoding TLR1 and TLR2 are co-integrated. The expression system may include controlling sequences not only inducing but also controlling the expression. When a preventive and therapeutic agent is used as drugs in the present invention, various prescribed compounds such as pharmaceutically acceptable normal carrier, bonding agent, stabilizing agent, excipient, diluent, pH buffer agent, disintegrator, solubilizer, dissolving adjuvant, isotonic agent can be added. As for a method for preventing or treating by using these drugs, preventive or therapeutic agents mentioned above with appropriate dose according to the patient's sex, body weight, symptoms can be administered orally or parenterally. In other words, it can be administered orally in a dosage form used generally, for example in form of powder, granule, capsules, syrup, suspension and the like, or parenterally for example in form of solution, emulsion, suspension and the like by injection, and moreover, it can be administered in nostril in form of spray.

The present invention will be explained in detail in the following by referring to the examples, but the technical scope of the present invention will not be limited to these.

REFERENCE EXAMPLE

Preparation of TLR2 Knockout Mice

TLR2 genes were screened from 129/SvJ murine genomic library (Stratagene) by using a probe from mouse EST clones, similar to human-TLR2 genes, subcloned in pBluescript vector (Stratagene), and were identified by restriction enzyme mapping and determination of DNA sequence. A targeting vector was constructed by replacing 1.3 kB of the gene fragment a portion of an exon containing the intracellular domain of TLR2 with pMC1-neo having poly A signal (Stratagene). The targeting vector has 4.8 kB if the 5' genomic fragment and 1.0 kb of the 3' genomic fragment as franking-sequence, and includes HSV-tk cassette at 5' end. The targeting vector was linearized with SalI and electroporated into E14.1 embryonic cells (ES cells). From the electroporated ES cells mentioned above, cells showing resistance to G418 and Gancyclovir and containing mutant TLR2 allele were screened. The ES cells were microinjected into C57BL/6 mouse blastocysts to generate chimeric mice. The male chimeric mice were bred to C57BL/6 female, and TLR2 knockout mice were obtained (Immunity 11, 443-451, 1999).

EXAMPLE 1

Preparation of TLR1 Knockout Mice

Figure 1:
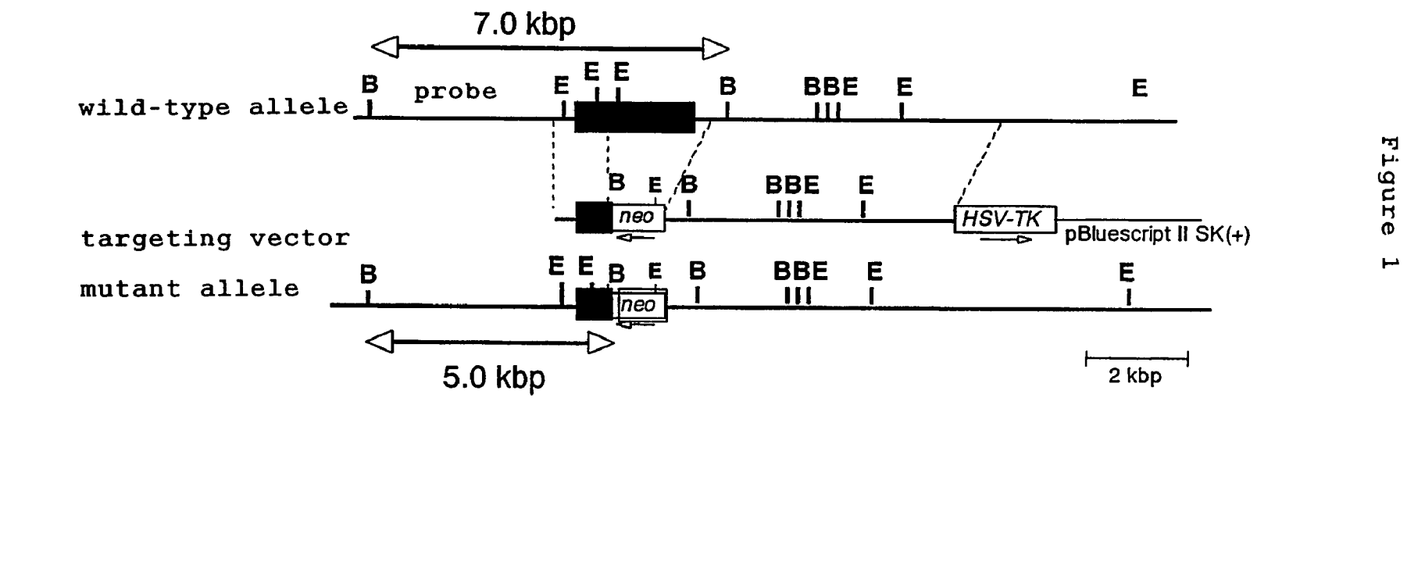
FIG. 1 is a figure that shows a genomic locus of the TLR1 knockout mouse of the present invention, of a wild-type mouse and of a targeting vector.

TLR1 genes were screened from 129Sv murine genomic library (Clontech) by using a probe derived from mouse TLR1 gene, subcloned in pBluescript II SK(+) vector and were identified by restriction enzyme mapping and DNA sequence determination. A targeting vector was constructed by replacing a gene site encoding mouse TLR1 intracellular domain and transmembrane domain (1.0 kB of the 5' end and 10 kb of the 3' end of a portion of an exon containing amino acid 575-795 of the mouse TLR1) with a neomycin cassette (Stratagene), and by introducing herpes simplex virus thymidine kinase (HSV-TK) as a negative selection marker (FIG. 1). The targeting vector was linearized with SalI, electroporated into E14.1 embryonic stem cells (ES cells). 125 clones showing resistance to G418 and gancyclovir were selected and three clones were screened by PCR and Southern blot methods.

Figure 2:
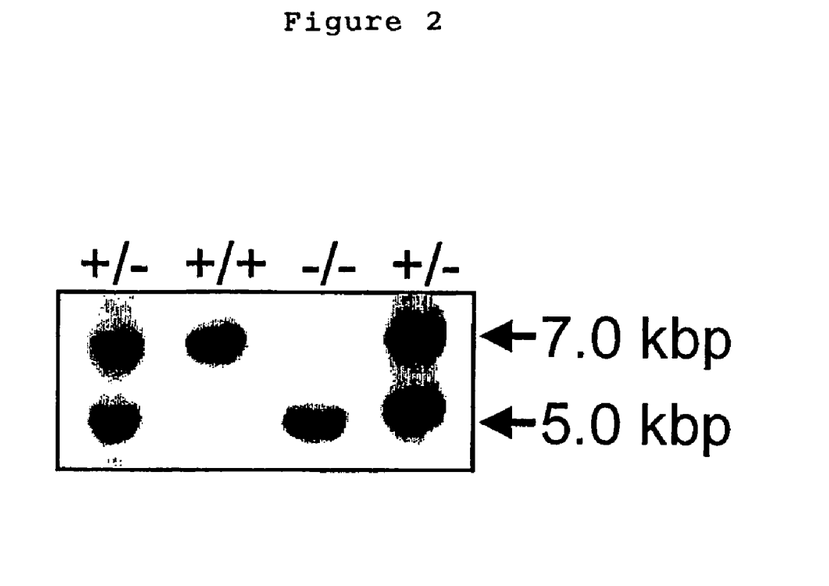
FIG. 2 is a picture that shows the result of Southern blot analysis of the TLR1 knockout mouse of the present invention.
Figure 3:
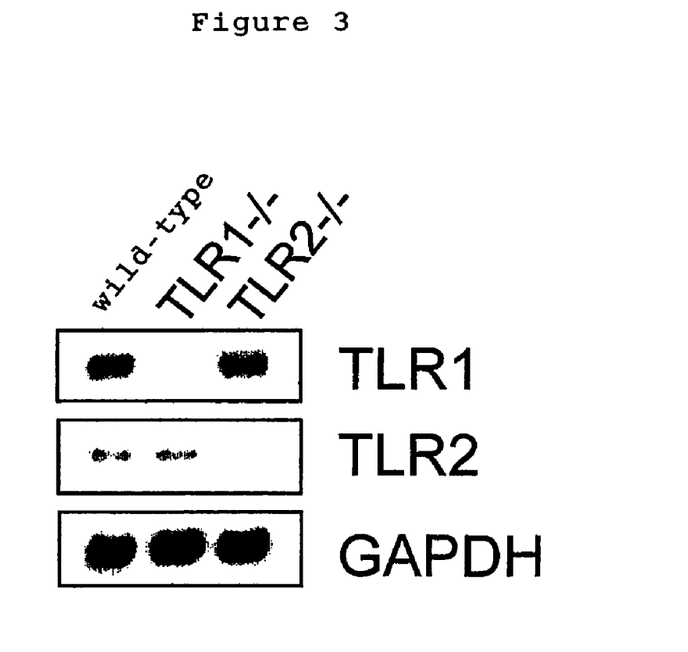
FIG. 3 is a picture that shows the result of Northern blot analysis of the TLR1 knockout mouse of the present invention.

Three targeted ES clones containing mutant TLR1 allele were microinjected into C57BL/6 blastocysts to generate chimeric mice. The male chimeric mice were bred with C57BL/6 female mice to generate heterozygotes F1 mice. By intercrossing the heterozygous F1 mice, homozygous mice (TLR1 knockout mice: $TLR^{-/-}$) were obtained. Homozygous mice were confirmed by digesting each genomic DNA extracted from murine tail with EcoRI, by Southern blot method by using a probe as shown in FIG. 1 (FIG. 2). Peritoneal macrophages of $TLR1^{-/-}$ mice did not express mRNA of TLR1 (FIG. 3). On the contrast, expression of TLR2 in $TLR^{-/-}$ macrophages was normal compared with the case of wild-type cells. $TLR1^{-/-}$ of the present invention were produced according to Mendel's law, and the mice were healthy, fertile and did not show any obvious abnormalities for the first six months. Moreover, there were no changes in thymocytes and splenocytes of $TLR1^{-/-}$ mice.

EXAMPLE 2

Preparation of Peritoneal Macrophages and Enzyme Linked Immunosorbent Assay 2 ml of 4% thioglycollate medium (DIFCO) were intraperitoneally injected into wild-type mice, TLR1 knockout ($TLR1^{-/-}$) and TLR2 knockout ($TLR2^{-/-}$) mice. Three days later, peritoneal exudate cells were isolated from each peritoneal cavity. The cells were cultured for 2 h at 37° C. in RPMI 1640 medium (Nacalaitesque) supplemented with 10% fetal bovine serum, cultured peritoneal macrophages ($5 \times 10^4$) and were stimulated with indicated bacterial components such as lipoprotein for 24 h. Concentration of TNFα (Genzyme Techne) and IL-6 (R&D) in culture supernatants were determined by enzyme linked immunosorbent assay (ELISA).

(Response to PAMPs)

Figure 4:
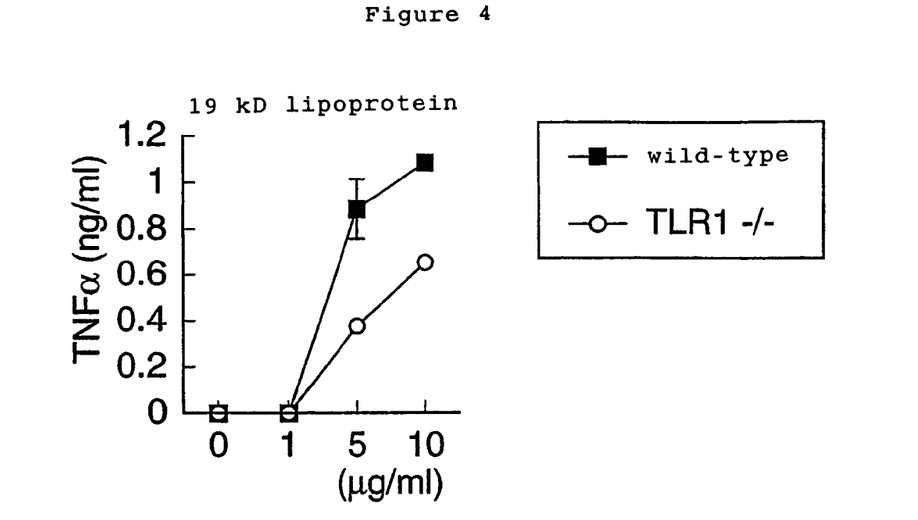
FIG. 4 is a figure that shows the result of TNFα production by 19 kD lipoprotein stimulation in TLR1 knockout mouse of the present invention and in a wild-type mouse.
Figure 5:
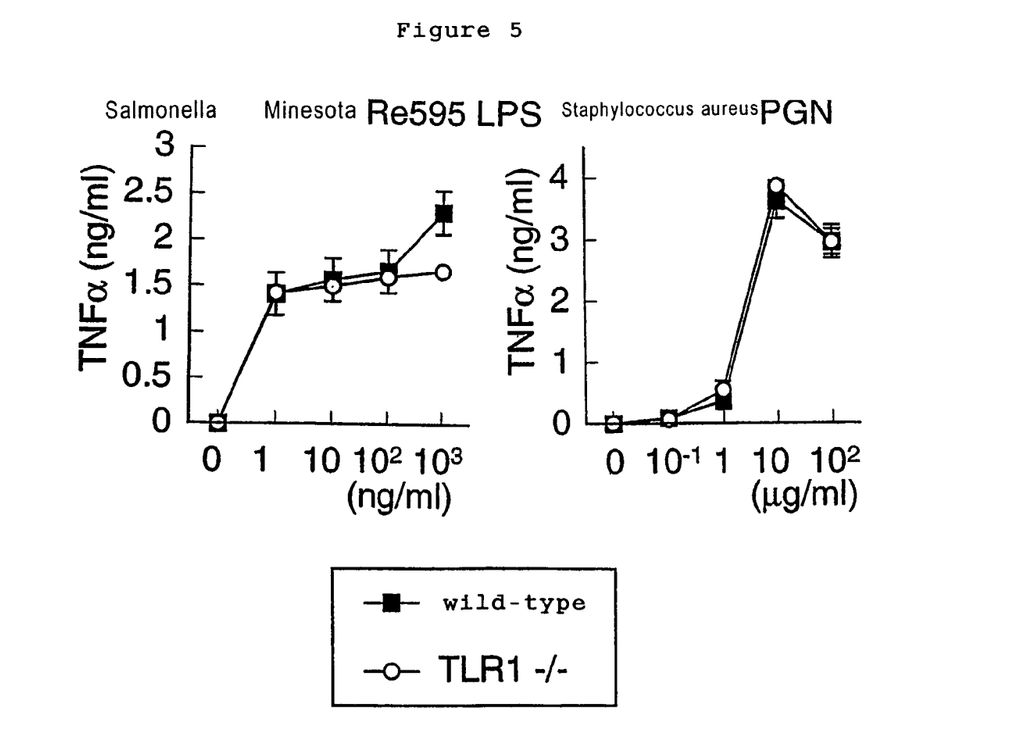
FIG. 5 is a figure that shows the result of TNFα production by LPS and PGN stimulation in the TLR1 knockout mouse of the present invention and in a wild-type mouse.
Figure 6:
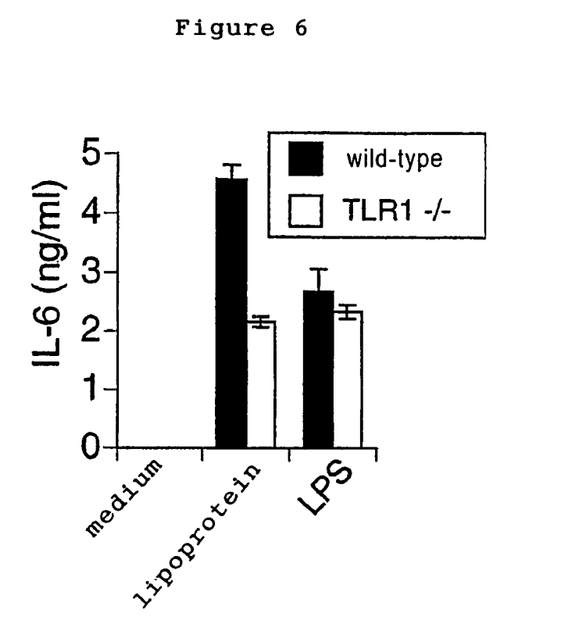
FIG. 6 is a figure that shows the result of IL-6 production responding to lipoprotein, LPS stimulation in the TLR1 knockout mouse of the present invention and in a wild-type mouse.
Figure 7:
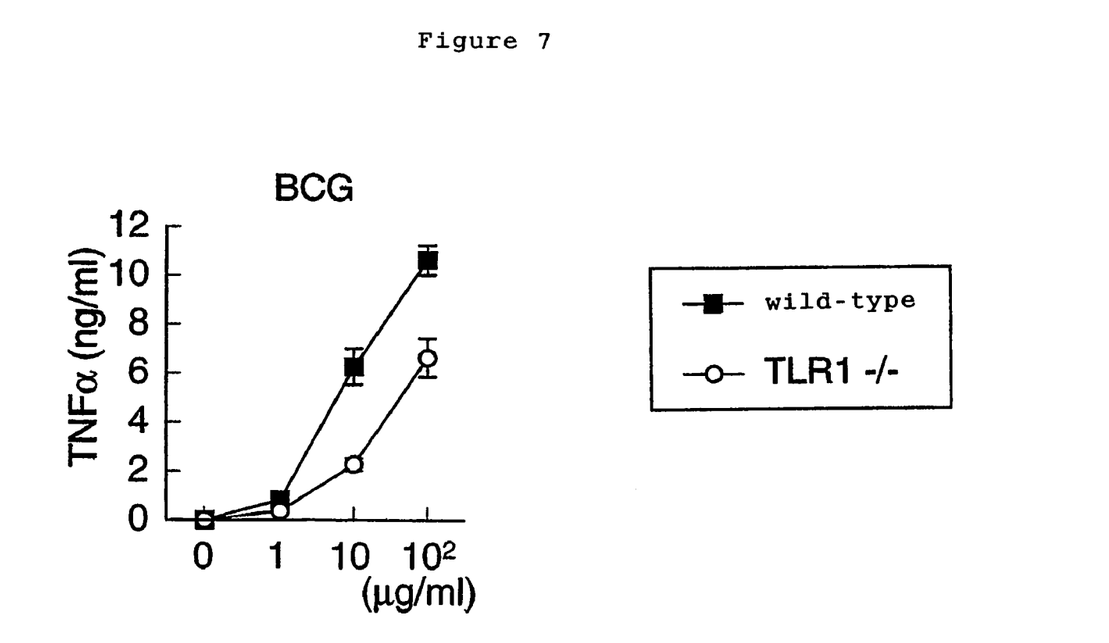
FIG. 7 is a figure that shows the result of TNFα production by BCG stimulation in the TLR1 knockout mouse of the present invention and in a wild-type mouse.

Native 19-kD lipoprotein purified from *Mycobacterium tuberculosis* (purified as described in Science 285, 732, 1999), LPS of *Salmonella minnesota* RE595, and PGN of *Staphylococcus aureus* were usedf or PAMPs. Peritoneal macrophages of wild-type and $TLR1^{-/-}$ mice stimulated with thioglycollate were cultured for 24 h in the presence of these PAMPs. Concentration of TNFα in culture supernatants was determined. The results of the use of nature 19 kD lipoprotein are shown in FIG. 4, and those of the use of LPA and PGN are shown in FIG. 5. Wild-type macrophages responded to 19 kD lipoprotein and generated TNFα in a dose-dependent manner, whereas TNFα production by TLR1$^{-/-}$ macrophages was impaired when stimulated with concentration of 5 μg/ml and 10 μg/ml of lipoprotein in the experiments (FIG. 4). On the other hand, when stimulated with LPS and PGN, TLR1$^{-/-}$ macrophages produced TNFα in a dose-dependent manner, almost at the same extent as those from wild-type cells (FIG. 5). Moreover, cultured peritoneal macrophages (5×10$^4$) were stimulated with native 19 kD lipoprotein and LPS for 24 h respectively, and concentration of IL-6 in culture supernatants was determined. As it is clear from the results shown in FIG. 6, IL-6 production responding to native 19-kD lipoprotein was lower in TLR1$^{-/-}$ macrophages compared with that of wild-type cells, whereas IL-6 production responding to LPS did not show significant difference between these two. Furthermore, to investigate whether TLR1 is engaged with recognition for all Mycobacteria, peritoneal macrophages were stimulated with *M. bovis* BCG (Kyowa), viable cells whose level were gradually increased for 24 h, and concentration of TNFα in culture supernatants was determined. The ability to generate TNGα in response to BCG was partially impaired in TLR1$^{-/-}$ macrophages as shown in FIG. 7. From these results, it was revealed that TLR1 is involved also with the recognition of 19 kD lipoprotein purified from Mycobacteria, and not only with viable Mycobacteria cells.

(Response to Synthetic Acylated Lipopeptide)

Figure 8:
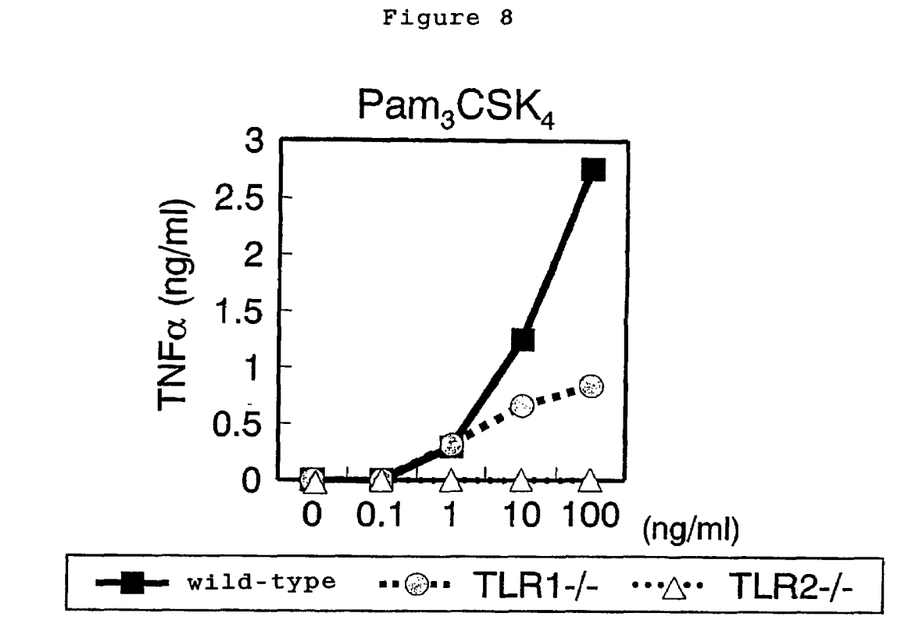
FIG. 8 is a figure that shows the result of TNFα production by $Pam_3CSK_4$ stimulation in the TLR1 knockout mouse of the present invention, in a TLR2 knockout mouse and in a wild-type mouse.
Figure 9:
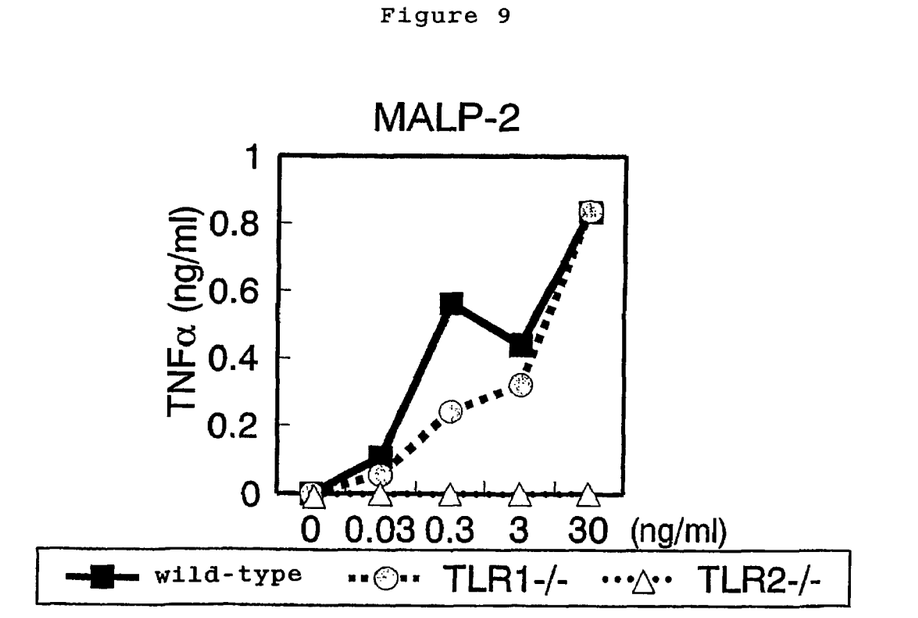
FIG. 9 is a figure that shows the result of TNFα production by MALP-2 stimulation in the TLR1 knockout mouse of the present invention, in a TLR2 knockout mouse and in a wild-type mouse.

Furthermore, the present inventors have previously shown that TLR2 is essential for both tri- and di-acylated lipopeptide response, and that TLR6 interacts with TLR2 and specifically recognizes di-acylatedlipopeptide (Int. Immunol. 13, 933, 2001). Cytokine production in response to 19 kD lipoprotein preparation was inhibited in TLR2$^{-/-}$ macrophages (Science 291, 1544, 2001). These results all show that TLR1 interacts also with TLR2, and recognizes tri-acylated lipoprotein. To elucidate chemical structure that TLR1 recognizes, peritoneal macrophages of wild-type and TLR1$^{-/-}$ mice were stimulated with Pam$_3$CSK$_4$, the synthetic bacterial tri-acylated peptide, and MALP-2, the synthetic Mycoplasmal di-acylated peptide, respectively. TLR1$^{-/-}$ macrophages showed significantly impaired TNFα production in response to Pam$_3$CSK$_4$ compared to wild-type cells (FIG. 8), whereas TLR1$^{-/-}$ cells responded normally to MALP-2 (FIG. 9). These results indicate that TLR1 is involved in the recognition of tri-acylated bacterial lipoprotein. In addition, TLR 1 differentially recognizes TLR2 ligands, distinguishing the degree of acylation of the lipopeptide.

EXAMPLE 3

Control of NF-κB Activity in Response to Lipopeptide Stimulation Due to Co-Expression of TLR1, TLR2 and TLR6

Figure 10:
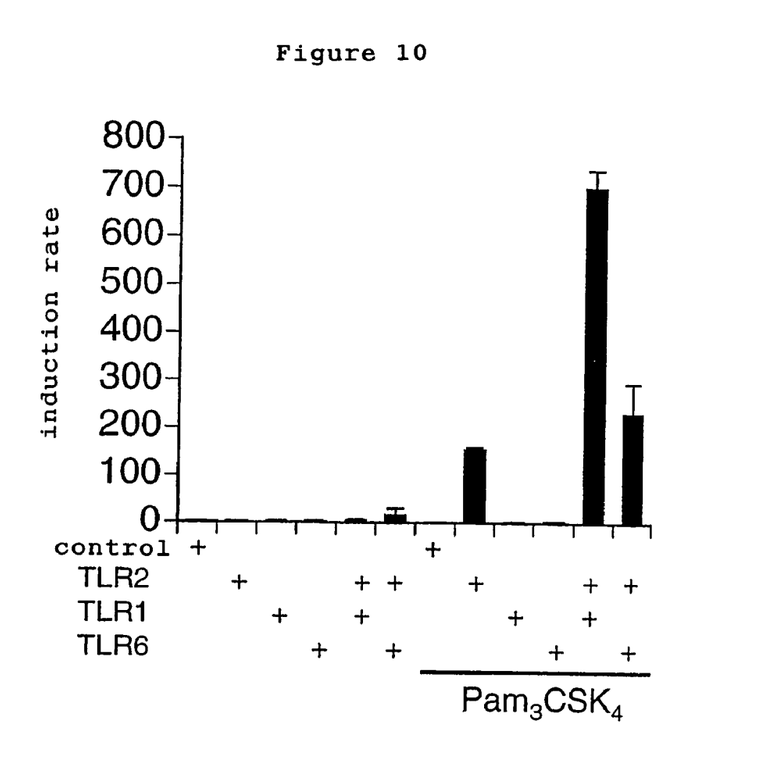
FIG. 10 is a figure that shows the result of NF-κB activation induced by $Pam_3CSK_4$ stimulation from co-expression of TLR1 of the present invention, TLR2 and TLR6.

HEK 293 cells were transformed with TLR1, TLR2 and TLR6 expression vectors, and pELAM-luciferase reporter plasmid were used together. For normalization of transfection efficiency by lipofectamine 2000 (Invitrogen), the indicated vector was used with pELAM-luciferase reporter plasmid (J. Bio. Chem. 274, 10689, 1999) and pRL-TK (Promega) to transfect transiently human fetal kidney (HFK)-293 cells. 24 h after transfection, the cells were stimulated with 10 ng/ml of Pam$_3$CSK$_4$ for 8 h. Then, the cells were lysed, and luciferase activity was measured by using Dual-luciferase reporter assay system (Promega) according to the manufacturer's instruction. The results are shown in FIG. 10. The expression of TLR2 conferred the NF-κB activation in response to Pam$_3$CSK$_4$ stimulation, and co-expression of TLR1 significantly enhanced the activation. In contrast, co-expression of TLR6 and TLR2 did not augment the NF-κB activation induced by Pam$_3$CSK$_4$ stimulation. These results indicate that TLR1 and TLR2, but not TLR6, are involved in the cooperative recognition of Pam$_3$CSK$_4$.

EXAMPLE 4

Interaction of TLR1 and TLR2 in Mammalian Cells

HEK293 cells were co-transfected with 3 μg Flag-tagged TLR2, TLR4 or 6 μg HA-tagged TLR1. After 36 h, the cells were lysed in the lysis buffer containing 1.0% Nonidet P-40, 150 mM NaCl, 20 mM tris-HCl (pH 7.5), 5 mM EDTA and aprotease inhibitor cocktail tablet, Complete (Roche Diagnostics). The solution was pre-treated for 1 h with protein G-sepharose, and immunoprecipitated for 12 h by using 2 μg anti-Flag M2 antibody or 2 μg anti-HA 12 CA5 antibody. The beads were washed four times in the lysis buffer, and the immunoprecipitated proteins were eluted in SDS-PAGE sample buffer solution, separated on SDS-PAGE and transferred onto PVDF membrane. HA-tagged TLR1 was detected with anti-HA antibody (Roche Diagnostics) and HRP-tagged anti-mouse Ig antibody. Flag-tagged proteins were identified with the second antibody, HRP-conjugated anti-Flag M2 antibody. Then, the antibodies were detected by enhanced chemiluminescence system (Dupont).

Figure 11:
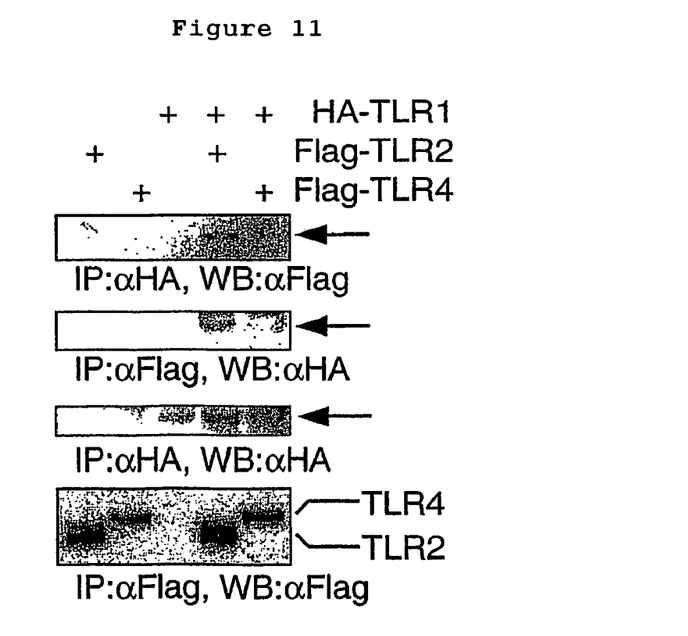
FIG. 11 is a figure that shows the result of the immunoprecipitation of HA-labeled TLR1 of the present invention.

Immunoprecipitation of HA-tagged TLR1 resulted in co-precipitation of Flag-tagged TLR2, but not of TLR4. Reciprocally, HA-tagged TLR1 also co-precipitated with Flag-tagged TLR2 (FIG. 11). However, stimulation with Pam$_3$CSK$_4$ did not affect the extent of association between TLR1 and TLR2. These results suggest that TLR1 and TLR2 associate in a ligand independent manner.

EXAMPLE 5

Lipopeptides Recognized by TLR1 and TLR2

Though the response to Pam$_3$CSK$_4$ was significantly impaired in TLR1$^{-/-}$ mice, the present inventors observed TLR1-independent cytokine production. To further screen the specific ligands recognized by TLR1, lipopeptides bearing different combination of fatty acids at their N-terminus were synthesized. The method for synthesizing synthetic N-palmitoyl-S-dipalmitoyl glyceryl (Pam$_3$) CSK$_4$ and MALP-2 are described previously (Science 285, 736, 1999; J. Immunol. 164, 554, 2000). JBT3002, a synthetic lipoprotein analogue, is as described previously (J. Leukoc. Biol. 63, 766, 1998). Further, other lipopeptides having different N-terminus acylation function (Peptide Institute Inc.) such as N-palmitoyl-S-dilauryl glyceryl (N-Pam-S-Lau$_2$)CSK$_4$, N-lauryl-S-dilauryl gylceryl (Lau$_3$)CSK$_4$, N-myristyl-S-dimyristyl glyceryl (Myr$_3$) CSK$_4$ were used. These differ in the length of fatty acid substituted on the N-terminus cysteine of the peptides. The lipid moiety of N-Pam-S-Lau$_2$CSK$_4$ and JBT3002 are the same.

Figure 12:
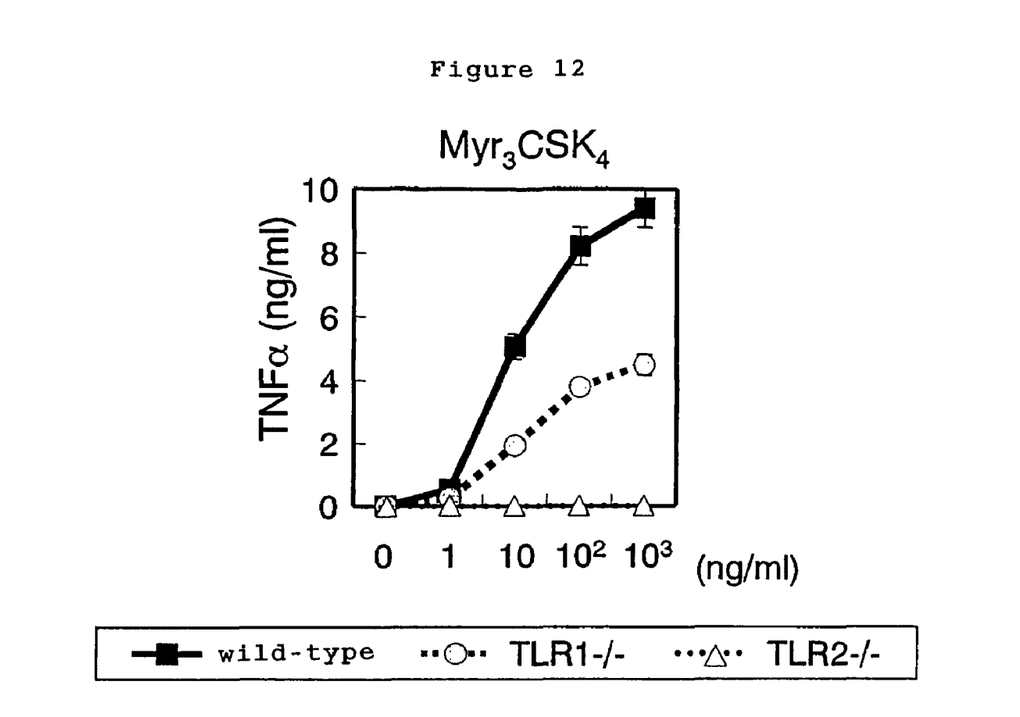
FIG. 12 is a figure that shows the result of TNFα production by $Myr_3CSK_4$ stimulation in the TLR1 knockout mouse of the present invention, in a TLR2 knockout mouse and in a wild-type mouse.
Figure 13:
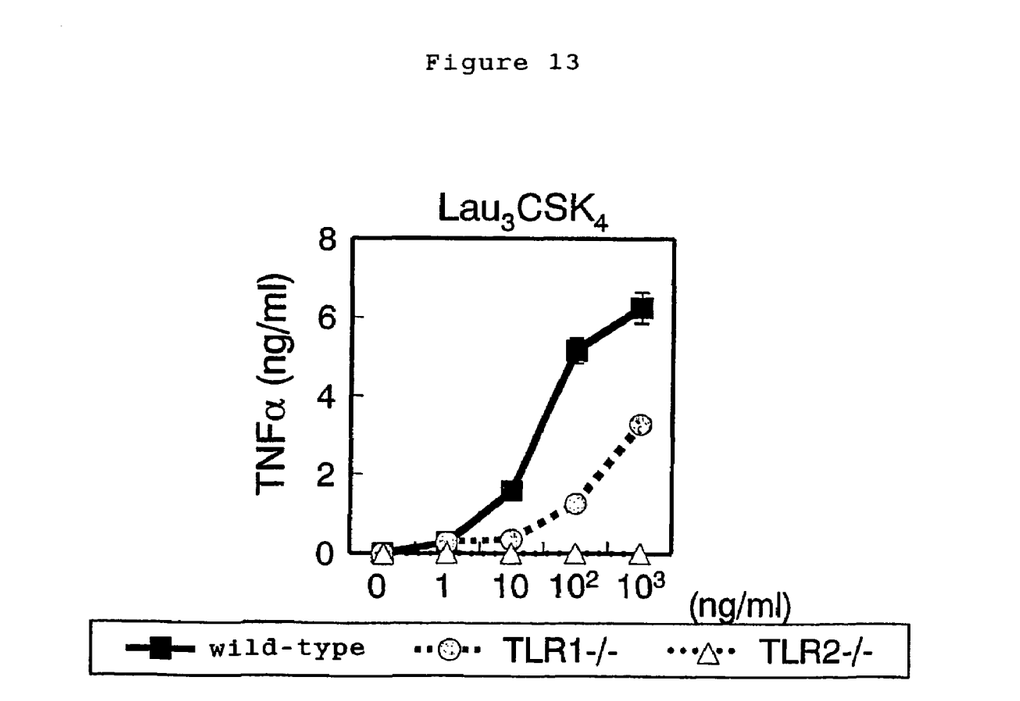
FIG. 13 is a figure that shows the result of TNFα production by $Lau_3CSK_4$ stimulation in the TLR1 knockout mouse of the present invention, in a TLR2 knockout mouse and in a wild-type mouse.
Figure 14:
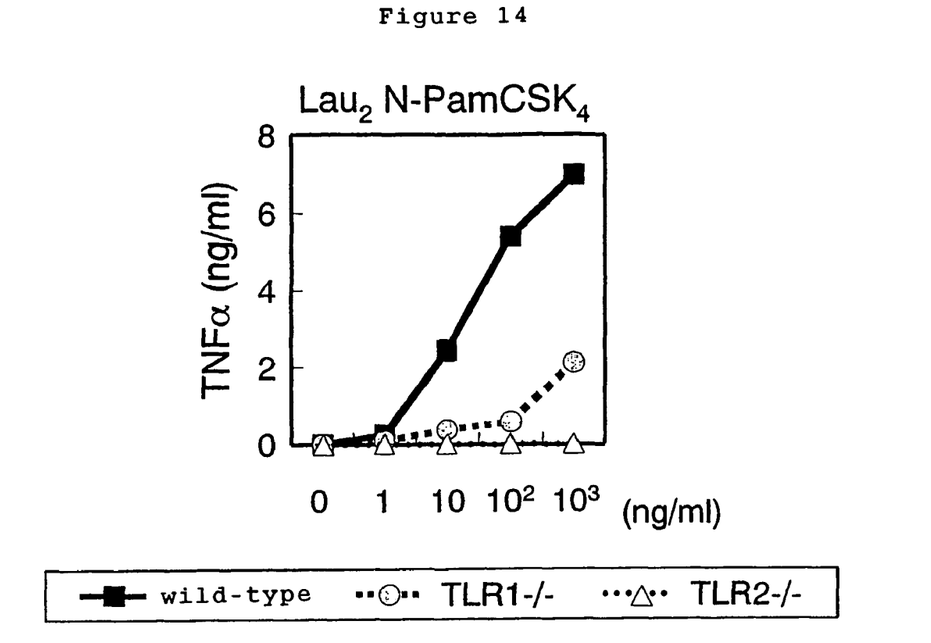
FIG. 14 is a figure that shows the result of TNFα production of $Lau_2N$-$PamCSK_4$ stimulation in the TLR 1 knockout mouse of the present invention, in a TLR2 knockout mouse and in a wild-type mouse.
Figure 15:
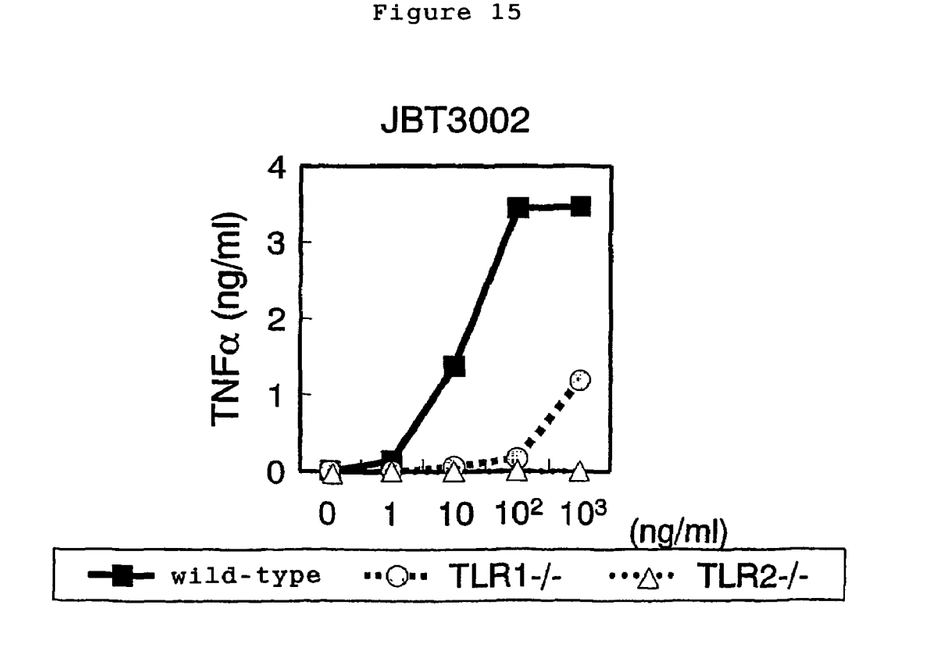
FIG. 15 is a figure that shows the result of TNFα production by JBT3002 stimulation in the TLR1 knockout mouse of the present invention, in a TLR2 knockout mouse and in a wild-type mouse.

Macrophages from wild-type, TLR1$^{-/-}$ and TLR2$^{-/-}$ mice were stimulated with the above-mentioned syntehtic peptide compounds, Myr$_3$CSK$_4$, Lau$_3$CSK$_4$, Lau$_2$N-PamCSK$_4$ and JBT3002, and the TNFα production was measured. The results are shown in FIGS. 12 to 15, respectively. All of these synthetic peptides activated wild-type cells to produce TNFα in a dose-dependent manner. Macrophages from TLR2$^{-/-}$ mice did not produce any detectable TNFα response to either of these lipopeptides. Macrophages from TLR1$^{-/-}$ impaired the production ability of TNFα in response to Myr$_3$CSK$_4$ and Lau$_3$CSK$_4$ (FIGS. 12 and 13). The ability of TLR1$^{-/-}$ cells to produce TNFα was considerably impaired when stimulated with Lau$_2$N-PamCSK$_4$ or JBT3002. This indicates that a subtle difference in lipid moiety of lipoprotein is critical for the recognition of TLR1 (FIGS. 14 and 15). These results provided evidence that TLR1 is involved in the recognition of tri-acylated lipoprotein as well as mycobacterial products. TLR1 and TLR2 cooperate to detect Pam$_3$CSK$_4$, by interacting each other, indicating that TLR2 pairs with TLR1 or TLR6 to recognize different PAMPS.

INDUSTRIAL APPLICABILITY

As the non-human animal models non-responsive to mycobacterial lipoproteins/lipopeptides such as TLR1 of the present invention are only non-responsive to mycobacterial lipoproteins/lipopeptides, by using this non-human animal model it would be possible to screen substances promoting or suppressing mycobacterial infections such as pulmonary tuberculosis, or substances promoting or suppressing the responsiveness to mycobacterial lipoproteins/lipopeptides such as agonists or antagonists to TLR1, and therefore to obtain new useful information to elucidate the molecule structure of bacterial infections such as mycobacterial species.

The invention claimed is:

1. A transgenic mouse whose genome comprises a homozygous inactivation of the Toll-like Receptor 1 (TLR1) gene; said TLR1 gene encoding a polypeptide that recognizes triacylated mycobacterial lipoproteins; wherein peritoneal macrophages of the mouse, also comprising a homozygous inactivation of the TLR1 gene, exhibit decreased responsiveness to triacylated mycobacterial lipoproteins.

2. A method for screening substances that promote or suppres a response to triacylated mycobacterial lipoproteins comprising contacting peritoneal macrophages isolated from the transgenic TLR-1 inactivated mouse of claim 1, which exhibits a decreased responsiveness to triacylated mycobacterial lipoproteins, with a substance, contacting peritoneal macrophages isolated from a wild-type control mouse with said substance, and comparing the response between the TLR-1 inactivated peritoneal macrophages and the control macrophages, wherein an increase in said responsiveness in comparison to the control is indicative of a substance that promotes a response to a mycobacterial lipoprotein/lipopeptide in a TLR-1 independent manner and wherein a greater decrease in responsiveness to a mycobacterial lipoprotein/lipopeptide in comparison to a wild-type control mouse is indicative of a substance that inhibits a response to a mycobacterial lipoprotein/lipopeptide in a TLR-1 independent manner.

* * * * *